(12) United States Patent
Schulz

(10) Patent No.: US 6,765,282 B2
(45) Date of Patent: Jul. 20, 2004

(54) SEMICONDUCTOR STRUCTURE AND METHOD FOR DETERMINING CRITICAL DIMENSIONS AND OVERLAY ERROR

(75) Inventor: Bernd Schulz, Radebeul (DE)

(73) Assignee: Advanced Micro Devices, Inc., Austin, TX (US)

(*) Notice: Subject to any disclaimer, the term of this patent is extended or adjusted under 35 U.S.C. 154(b) by 0 days.

(21) Appl. No.: 10/134,564

(22) Filed: Apr. 29, 2002

(65) Prior Publication Data

US 2003/0042579 A1 Mar. 6, 2003

(30) Foreign Application Priority Data

Aug. 30, 2001 (DE) .......................................... 101 42 318

(51) Int. Cl.[7] .............................................. H01L 23/58
(52) U.S. Cl. .................... 257/629; 257/629; 356/388; 356/3; 356/237.1; 438/14
(58) Field of Search ................................ 257/629, 632, 257/635, 636; 356/445, 376, 351, 357, 388, 237.1, 3, 630, 631, 632, 625, 601, 622, 399, 400, 401, 369; 430/30; 438/14

(56) References Cited

U.S. PATENT DOCUMENTS

| | | | |
|---|---|---|---|
| 5,867,276 A | 2/1999 | McNeil et al. .............. 356/445 |
| 5,877,276 A | 3/1999 | Borden ........................ 356/376 |
| 5,880,838 A | 3/1999 | Marx et al. .................. 356/351 |
| 6,051,348 A | 4/2000 | Marinaro et al. ............. 430/30 |
| 6,081,334 A | 6/2000 | Grimbergen et al. ........ 356/357 |
| 6,245,584 B1 | 6/2001 | Marinaro et al. ............. 438/14 |

Primary Examiner—Nathan J. Flynn
Assistant Examiner—Pershelle Greene
(74) Attorney, Agent, or Firm—Williams, Morgan & Amerson

(57) ABSTRACT

A semiconductor structure and a method of determining an overlay error produced during formation of the semiconductor structure are disclosed. The semiconductor structure comprises a first two-dimensional periodic pattern and a second two-dimensional periodic pattern, which overlap with each other, wherein a relative position between the overlapping first and second two-dimensional periodic patterns indicates the magnitude and direction of an overlay error caused during the formation of the first and second two-dimensional periodic patterns. The semiconductor allows one to independently determine the overlay errors in linearly independent directions by directing a light beam of known optical properties onto the first and second two-dimensional periodic patterns and by analyzing the diffracted beam by comparison with reference data.

23 Claims, 3 Drawing Sheets

SEMICONDUCTOR STRUCTURE AND METHOD FOR DETERMINING CRITICAL DIMENSIONS AND OVERLAY ERROR

BACKGROUND OF THE INVENTION

1. Field of the Invention

The present invention relates to the field of fabrication of integrated circuits, and, more particularly, to a semiconductor structure and a method for determining critical dimensions and an overlay error caused during the formation of two subsequent material layers.

2. Description of the Related Art

Fabrication of integrated circuits requires tiny regions of precisely controlled size to be formed in a material layer of an appropriate substrate, such as a silicon substrate. These tiny regions of precisely controlled size are generated by treating the material layer by means of, for example, ion implantation or etching, wherein a mask layer is formed over the material layer to be treated to define these tiny regions. In general, a mask layer may consist of or is formed by means of a layer of photoresist that is patterned by a lithographic process. During the lithographic process, the resist may be spin coated onto the wafer substrate, and is then selectively exposed to ultraviolet radiation. After developing the photoresist, depending on the type of resist, positive resist or negative resist, the exposed portions or the non-exposed portions are removed to form the required pattern in the photoresist layer. Since the dimensions of the patterns in modern integrated circuits are steadily decreasing, the equipment used for patterning device features have to meet very stringent requirements with regard to resolution of the involved fabrication processes. In this respect, resolution is considered as a measure specifying the consistent ability to print minimum-size images under conditions of predefined manufacturing variations. One dominant factor in improving the resolution is represented by the lithographic process, in which patterns contained in a photo mask or reticle are optically transferred to the substrate via an optical imaging system. Therefore, great efforts are made to steadily improve optical properties of the lithographic system, such as numerical aperture, depth of focus, and wavelength of the light source used.

The quality of the lithographic imagery is extremely important in creating very small feature sizes. Of comparable importance is, however, the accuracy with which an image can be positioned on the surface of the substrate. Integrated circuits are fabricated by sequentially patterning material layers, wherein features on successive material layers bear a spatial relationship to one another. Each pattern formed in a subsequent material layer has to be aligned to a corresponding pattern formed in the previous material layer within specified registration tolerances. These registration tolerances are caused by, for example, a variation of a photoresist image on the substrate due to non-uniformities in such parameters as resist thickness, baking temperature, exposure and development. Furthermore, non-uniformities in the etching processes can lead to variations of the etched features. In addition, there exists an uncertainty in overlaying the image of the pattern for the current material layer to the etched pattern of the previous material layer, while photolithographically transferring the image onto the substrate. Several factors contribute to the inability of the imagery system to perfectly overlay two layers, such as imperfections within a set of masks, temperature differences between times of exposure, and a limited registration capability of the alignment tool. As a result, the dominant criteria determining the minimum feature size finally obtained are resolution for creating features in individual substrate levels and the total overlay error to which the above-explained factors, in particular the lithographic processes, contribute.

Accordingly, it is essential to steadily monitor the resolution, i.e., the capability of reliably and reproducibly creating the minimum feature size, also referred to as critical dimension (CD), within a specific material layer, and to steadily determine the overlay accuracy of patterns of two subsequently formed material layers. Recently, scatterometry has become a powerful tool in characterizing a periodic pattern of features with a size in the range of 1 $\mu$m to 0.1 $\mu$m. In the scatterometry analysis, the substrate containing a periodic structure is illuminated with radiation of an appropriate wavelength range and the diffracted light is detected. Many types of apparatus may be used for illumination and detecting of the diffracted light beam. U.S. Pat. No. 5,867,276 describes a so-called two-$\theta$ scatterometer wherein the angle of incidence of a light beam is continuously varied by synchronously rotating the sample and the detector. Furthermore, this document describes a lens scatterometer system utilizing a rotating block to translate a light beam emitted from a light source to different points of the entrance aperture of a lens to illuminate the substrate at different angles of incidence. Moreover, this document describes a scatterometer with a fixed angle of incidence that utilizes a multi-wavelength illumination source to obtain the required information from the diffracted multi-wavelength beam. From this information contained in the measurement spectrum, the optical and dimensional properties of the individual elements that form the periodic structure and thickness of underlying films can be extracted, for example, by statistical techniques. The sample parameters of interest may include the width of lines, if the periodic pattern contains lines and spaces, their sidewall angle, and other structural details. In case of a more complex periodic structure having, for example, a two-dimensional periodicity, the parameters may include dimensional properties such as hole diameter or depth. It should be noted that in the present application the term "scatterometer" also includes devices emitting a substantially linearly polarized light beam such as an ellipsometer, to obtain structural information with respect to changes in the polarization state by detecting and analyzing the beam scattered from the periodic structure.

Although a scatterometer provides a powerful tool for a non-destructive and swift method for determining the quality of periodic structures formed in a material layer in conformity with semi-conductor fabrication processes, it is desirable to also determine the overlay accuracy by means of scatterometry.

SUMMARY OF THE INVENTION

According to one aspect of the present invention, a semiconductor structure for metrology of critical dimensions and overlay accuracy comprises a substrate having a surface defined by an X direction and a Y direction. Moreover, the semiconductor structure comprises a first periodic pattern formed on the substrate and having a first X periodicity along the X direction and a first Y periodicity along the Y direction. Additionally, the semiconductor structure comprises a second periodic pattern formed on the substrate and having a second X periodicity along the X direction and a second Y periodicity along the Y direction, wherein the first periodic pattern and the second periodic pattern overlap with each other and define an X overlap region indicating an overlay error in the X direction, and a Y overlap region indicating an overlay error in the Y direction.

According to another aspect of the present invention, a semiconductor structure for metrology of critical dimensions and overlay accuracy comprises a substrate having a surface defined by an X direction and a Y direction, and a two-dimensional periodic structure including a plurality of elementary cells. Moreover, each elementary cell comprises a first region and a second region, defining a first edge extending along the X direction and a second edge extending along the Y direction. Furthermore, the elementary cell comprises a third region formed in spaced relationship to the first and second regions and the third region defines a Y overlap region with the first and second region at the first edge and an X overlap region with the first and second regions at the second edge, wherein the X overlap region and the Y overlap region differ from each other in one of shape, total area, diffracting characteristics and optical characteristics.

According to yet another aspect of the present invention, a semiconductor structure for metrology of critical dimensions and overlay accuracy comprises a substrate having a surface defined by an X direction and a Y direction, a first periodic pattern formed on the substrate and a second periodic pattern formed on the substrate. The first and second periodic patterns overlap with each other and define a composed 2-dimensional diffraction pattern defined by a pitch DX along the X direction and a pitch DY along the Y direction, wherein DX and DY are determined by the relative position of the first and second periodic patterns.

According to still another aspect of the present invention, a method of determining an overlay error caused during formation of a semiconductor structure is provided. The method comprises providing the semiconductor structure that includes a substrate defining a first and a second direction and a first two-dimensional periodic pattern formed by a first lithographic process and a second two-dimensional periodic pattern formed by a second lithographic process, wherein the relative position of the first and second patterns to each other indicates an overlay error with respect to the first and second directions, respectively. Moreover, the method comprises directing a light beam onto the first and second two-dimensional periodic patterns, and detecting a light beam diffracted by the first and second two-dimensional periodic patterns to generate a measurement spectrum. In addition, the method comprises comparing the measurement spectrum with reference data, wherein the reference data represents information for a predefined overlay error of the first and second periodic patterns with respect to the first and second directions.

BRIEF DESCRIPTION OF THE DRAWINGS

The invention may be understood by reference to the following description taken in conjunction with the accompanying drawings, in which like reference numerals identify like elements, and in which.

Figure 1A:
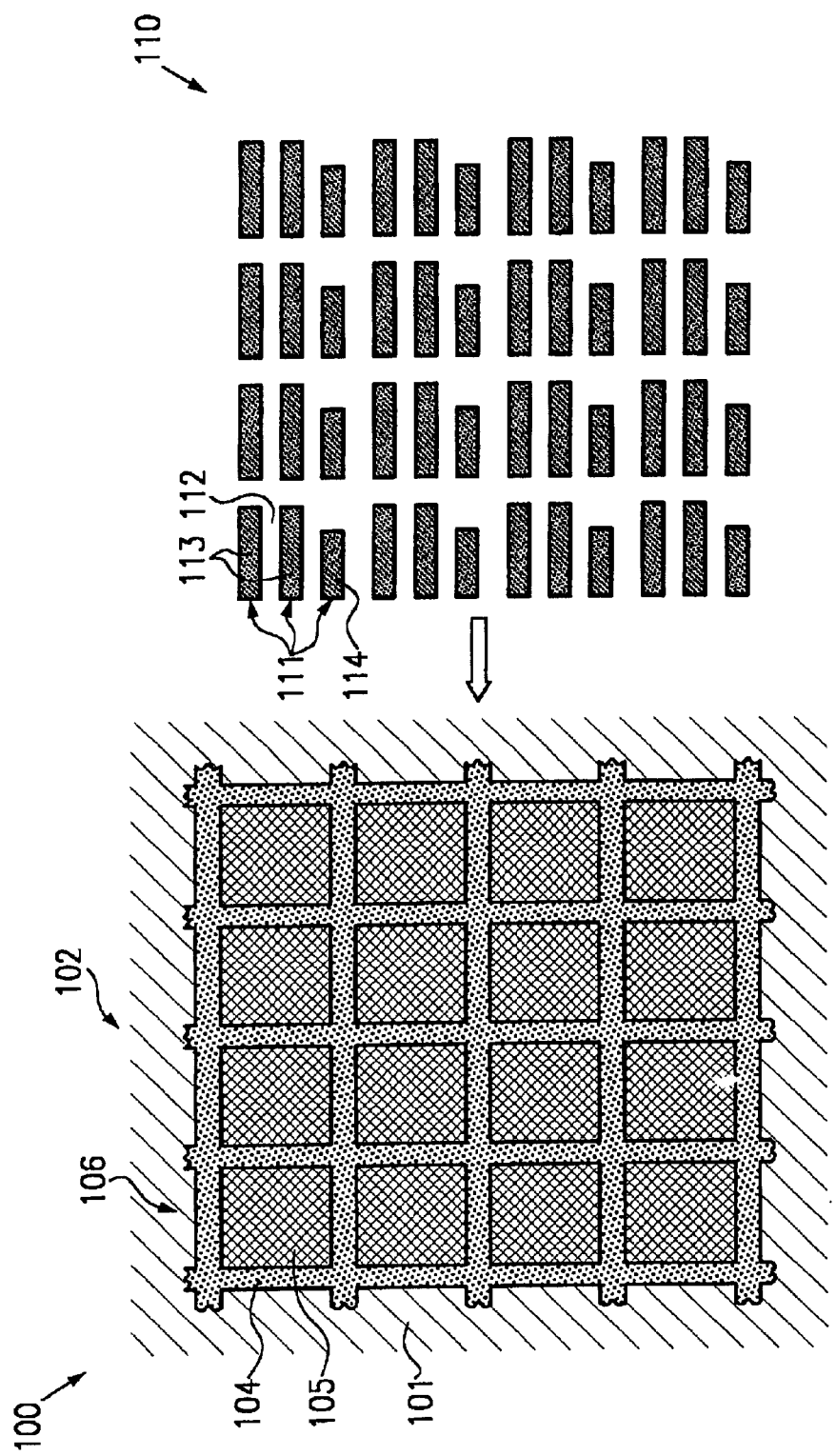
FIGS. 1a and 1b are schematic top views of one embodiment of a semiconductor structure suitable for determining an overlay accuracy of patterns that are formed by subsequent lithographic processes.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

As previously explained, a light beam diffracted by a periodic pattern exhibits an intensity distribution with respect to angle of incidence and/or direction of polarization and/or angle of deflection that will strongly depend on the diffracting characteristics of the periodic pattern. This effect is exploited to monitor, for example, critical dimensions of circuit features within a specific process level. The present invention is based on the inventor's finding that two overlapping periodic patterns that are formed by subsequent lithographic processes may bear information on the overlay error along two linearly independent directions. That is, by suitably overlapping two periodic patterns, a scatterometric measurement may not only yield the magnitude of an overlay error along two linearly independent directions, but will also yield the sign or direction (for example, −X, +X) of the overlay error independently in each of the two directions.

Figure 1B:
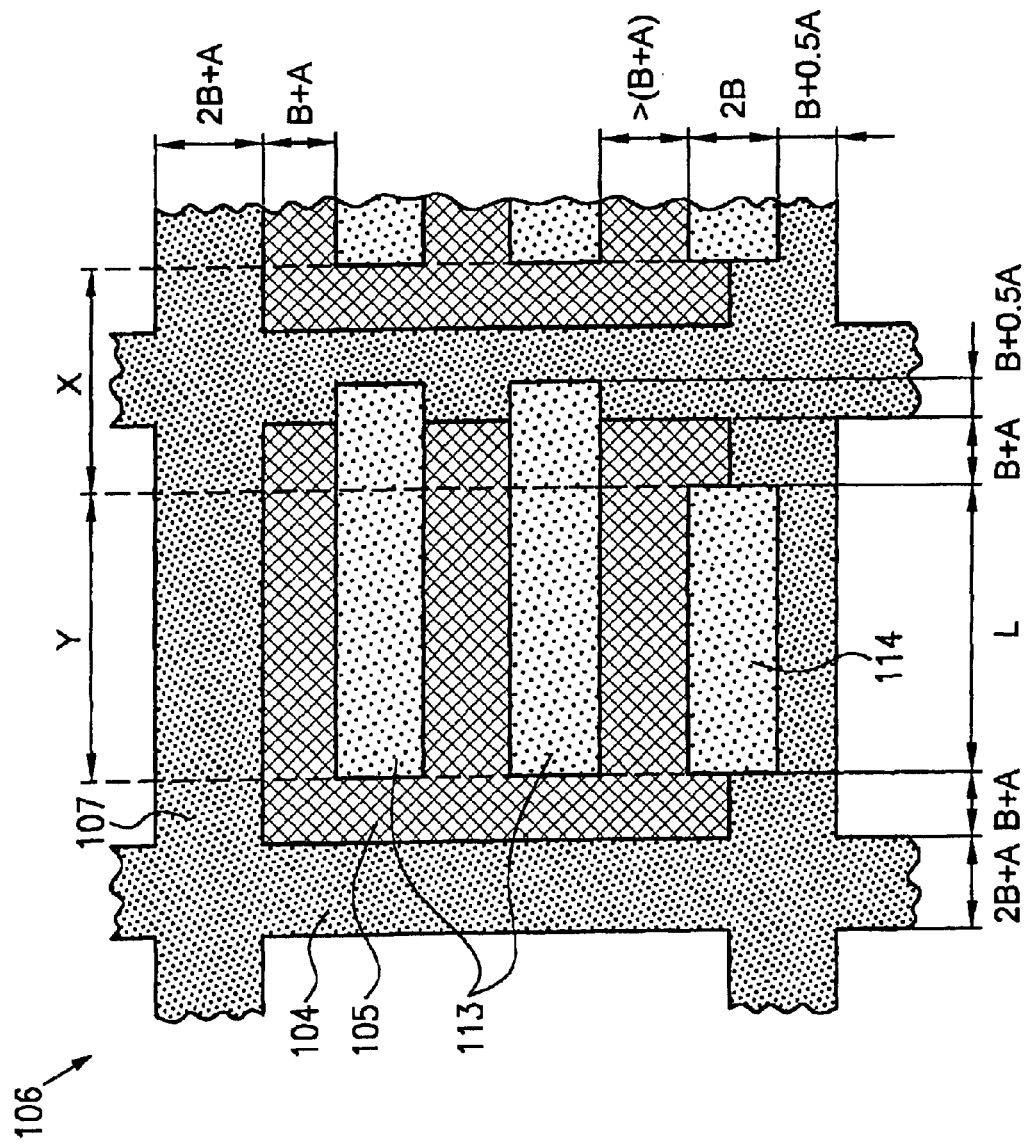

With reference to FIGS. 1a and 1b, an illustrative embodiment according to the present invention will now be described. In FIG. 1a, a semiconductor structure 100 comprises a substrate 101, for example, a substrate used for manufacturing integrated circuits, such as a silicon substrate, germanium substrate, a glass substrate, and the like. The substrate 101 may comprise a plurality of material layers with circuit features formed thereon, depending on a specific process level of the semiconductor structure 100. Above the substrate 101, a first periodic pattern 102 is formed that has an X-periodicity and a Y-periodicity along an X-direction and a Y-direction as indicated by the coordinate system depicted in FIG. 1a. The first periodic pattern 102 may be considered to be composed of a plurality of elementary cells 106 comprising a first region 104 and a second region 105. The first and second regions 104 and 105 have different optical characteristics for a variety of reasons, such as the first and second regions 104, 105 being formed of different types of material having different complex indices of refraction. Furthermore, the elementary cell 106 may have a varying surface profile corresponding to the first and second regions 104 and 105. For example, the first region 104 may be formed as lines having a specified width and a specified height, whereas the second region 105 may be formed as an opening or a recess depending on the required optical characteristics of the first periodic pattern 102. Likewise, the first region 104 may be formed as openings or recesses to create a varying surface profile of the elementary cell 106. The periodic difference between the first and second regions 104, 105 results in a two-dimensional periodicity that defines the diffracting characteristics of the periodic pattern 102. The number of elementary cells 106 depends on design rules and the available space on the substrate 101. In one embodiment, the periodic pattern 102 is located in a scribe lane that separates individual chip areas from each other.

Upon directing a light beam having known characteristics such as polarization state, angle of incidence, wavelength distribution, a light beam diffracted from the first periodic pattern 102 can be detected and analyzed to extract information about the diffracting characteristics of the first periodic pattern 102. In this respect, diffracting characteristics are meant to include geometrical factors such as the X periodicity and Y periodicity of the periodic pattern 102, height of features of the periodic pattern 102, sidewall angles of features, for example of the first region 104 when it is formed as a line, type of material of the first and second regions 104 and 105, and the like. The measurement spectrum finally obtained strongly depends on the diffracting characteristics of the first periodic pattern 102. A variation in one of the parameters determining the diffracting characteristics leads to a corresponding variation of one of the optical parameters of the diffracted beam, such as a variation of the polarization state with respect to the polarization state of the incoming light beam. The measurement spectrum is then compared to reference data that may be obtained by experiment, theoretically by modeling the first periodic pattern 102, e.g., by calculations based upon Maxwell's equations, or by a combination of both methods to obtain the required information on quality of the features defining the first periodic pattern 102.

In accordance with the present invention, a second periodic pattern 110 is formed above the substrate 101. For the sake of clarity, in FIG. 1a the first periodic pattern 102 and the second periodic pattern 110 are shown side-by-side, but in reality the periodic patterns 102 and 110 are formed such that they overlap with each other (FIG. 1b). The second periodic pattern 110 has a predefined X-periodicity and a Y-periodicity along the X-direction and the Y-direction, respectively. The second periodic pattern 110 is also comprised of a plurality of elementary cells 115. Each elementary cell 115 of the second periodic pattern 110 comprises a first region 111 and a second region 112. Regarding the properties of the first and second regions 111 and 112, the same criteria apply as given with reference to the first and second regions 104 and 105 of the first periodic pattern 102. In this example, the first regions 111 are represented by a plurality of first lines 113 and a second line 114, wherein the second line 114 is shorter than the first lines 113. The second regions 112 are formed as recesses or openings.

FIG. 1b shows a schematic top view of one elementary cell 106, wherein the first periodic pattern 102 and the second periodic pattern 110 overlap with each other. In the following, it is assumed that a maximum overlay error with respect to the X-direction and the Y-direction that may be created during the formation of the first periodic pattern 102 and the second periodic pattern 110 is given by B. Individual lines 107, defining the first region 104, have a width that is given by approximately 2×B+A, wherein A is a measure that is given by design rules of the specific process level. Typically, a maximum overlay error is in the range from approximately 20–50% of the critical dimension under consideration and the magnitude of the measurement A may be selected in the same order of magnitude as the maximum overlay error. For example, using present-day manufacturing technology, feature sizes, e.g., gate electrodes, may have a critical dimension of approximately 0.18 $\mu$m. Thus, in this example, the value of A may range from approximately 0.036–0.09 $\mu$m.

In this example, the lines 113 of the second periodic structure 110 have a length sufficient to allow them to overlap with one of the vertically oriented lines 107 by an amount of approximately B+0.5 A when the overlay error with respect to the X direction is assumed to be equal to zero. The line 114 of the second periodic structure 110 has a length that is less than the length of the lines 113 and is designed such that a distance from the line 114 to the vertically oriented lines 107 is approximately B+A when the overly error in the X direction equals zero. Thus, a maximal overlay error B in the X direction does not lead to an overlap of the vertically oriented lines 107 and the lines 114. The width of the lines 114 is selected to be approximately 2×B and the line 114 is located within the elementary cell 106 to overlap with respect to the Y direction with one of the horizontally oriented lines 107 with an amount equal to approximately B when a Y overlay error equals zero. Moreover, a minimum vertical distance between the lines 113 and the line 114 is greater than B+A, so that a relative shift of the first periodic pattern 102 with respect to the second periodic pattern 110 due to a Y overlay error will result in a maximum overlap of said one horizontally oriented line 107 and the line 114, but will not lead to an overlap of one of the lines 113 with a horizontally oriented line 107 of the first periodic pattern 102.

The subsequent formation of the first periodic pattern 102 and the second periodic pattern 110 will lead to an overlay error in the X and Y directions due to unavoidable inaccuracies during the photolithographic and patterning processes involved in forming the patterns 102 and 110. The amount of overlap of the vertically oriented lines 107 of the first pattern 102 and the lines 113 of the second pattern 110 is sensitive to the overlay error in the X direction independent of any shift in the Y direction. Likewise, the amount of overlap of the horizontally oriented line 107 and the line 114 only depends on the overlay error along the Y direction, regardless of a shift in the X direction. Thus, the amount of overlap with respect to the X direction and with respect to the Y direction will independently change the diffracting characteristics of the combined pattern consisting of the first periodic pattern 102 and the second pattern 110. The reason for this results from the fact that, for example, the vertically oriented edge of the line 107 and the second region 105 will experience a different modification or "disturbance" owing to the different sort of "edge effect" caused by the square-like overlap with lines 113 compared to the rectangular-like Y overlap of the horizontally oriented edge of the line 107 and the second region 105. It should be noted in this respect that the arrangement depicted in FIG. 1b may be varied in a number of ways. For example, two lines 113 overlapping with the vertically oriented line 107 are depicted. In a further illustrative embodiment, one or three or more lines may be provided in order to, for example, adjust the intensity of "response" created by the "edge effect" of X overlap to the intensity of "response" of the line 114 with the horizontally oriented line 107 in the diffracted beam. That is, the degree of change in the measurement spectrum caused by the overlap of the lines 113 in the X direction can be adjusted by providing more lines or less lines depending on the required degree of change in the spectrum. Moreover, to more clearly distinguish between changes in the spectrum caused by a variation of the X overlap or the Y overlap, by providing a plurality of lines 113, an additional "disturbance periodicity"

is created, defining a "fine" structure, that will facilitate the analysis of the measurement spectrum with respect to separation of the X overlay error and the Y overlay error. Moreover, the length of the line 114 may also be adjusted to conform with the response from the X overlap regions of the lines 113. Accordingly, the ratio of the number N of lines 113 and the length L of the line 114 can correspondingly be adjusted to obtain the desired degree of change in the measurement spectrum. Moreover, instead of simple lines 113 and 114, a more complex structure may be employed. For instance, the lines 113 may be represented by a via chain or by a row of vias or any other appropriate structure that preferably is also used in the circuit features in the residual area of the substrate 101. Moreover, lines 113 and 114 may be represented by openings or recesses formed in the second regions 112 of the second periodic structure 110 (see FIG. 1a).

The dimensions in the embodiment illustrated in FIG. 1 are selected so that for every possible overlay error within a defined maximum range of [+B, −B] changes of the overlap indicating the X overlay error will never contribute to changes of the overlap indicating the Y overlay error. Furthermore, using the present invention, the overlap regions maintain sensitivity to an overlay error within the predefined maximum overlay range, that is, the situations of no overlap at all or 100% overlap all the time are avoided. Considered from another point of view, the first periodic pattern 102 and the second periodic pattern 110 have the same approximate X and Y periodicities and are arranged such that they have a spatial "phase shift" that depends on the relative displacement of the first and second periodic patterns 102 and 110 to each other. Thus, the semiconductor structure 110 is sensitive to the absolute magnitude of overlay error as well as to the sign or direction (±X, ±Y) of the overlay error.

The second periodic pattern 110 may be formed by providing a patterned photoresist layer above the first periodic pattern 102 to monitor overlay accuracy of the photolithographic process. The second periodic structure 110 may also be formed by performing further patterning processes, such as etching, ion implantation, and the like that are necessary to establish the second periodic structure 110 in conformity to actual circuit features so as to monitor overlay accuracy of a portion or the entire patterning process for two process levels.

Figure 2:
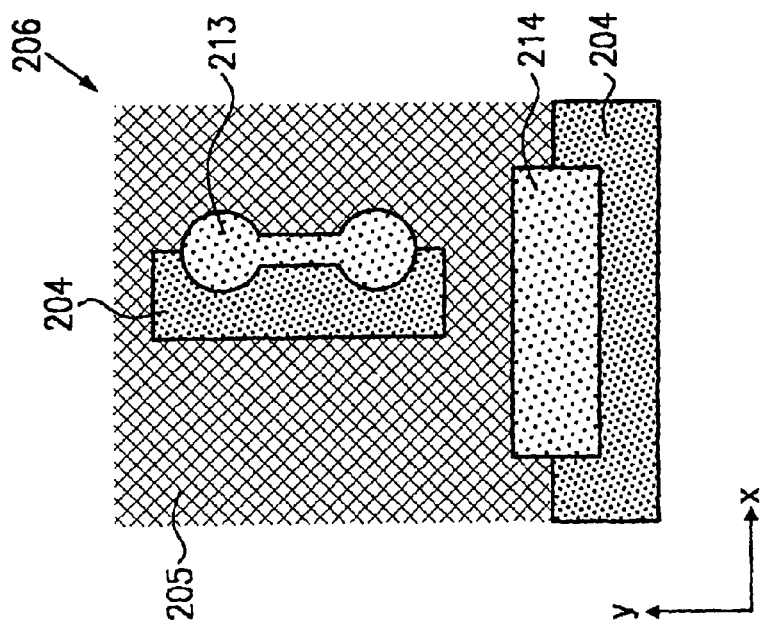
FIG. 2 shows a schematic top view of a further illustrative embodiment in accordance with the present invention.

FIG. 2 schematically shows a top view of a further illustrative embodiment of the present invention. FIG. 2 shows an elementary cell 206 defined by a first periodic pattern that is represented by first regions 204 and a second region 205, and a second periodic pattern represented by a third region 213 and a fourth region 214. The regions 204 may be lines of a first material that are embedded in the second region 205 formed of a second material. The third region 213 and the fourth region 214 may be formed by means of an additional photolithographic step and a subsequent patterning step, such as anisotropic etching, to create the third region 213 in the form of a via chain and the fourth region 214 in the form of a line. As in the embodiments explained with reference to FIGS. 1, the dimensions of the regions 204, 213 and 214 may preferably be selected so as to obtain 100% overlay sensitivity for a predefined maximum overlay error. As can be seen from FIG. 2, the elementary cell 206 is independently sensitive to a relative displacement of the third and second regions 213 and 214 with respect to the first regions 204. Particularly, the different types of shape of the third region 213 and the fourth region 214 result in a response in the measurement spectrum so as to easily identify a displacement in the X and Y direction, respectively, due to the different type of edge effect generated by the corresponding overlap regions, as is previously explained.

Figure 3:
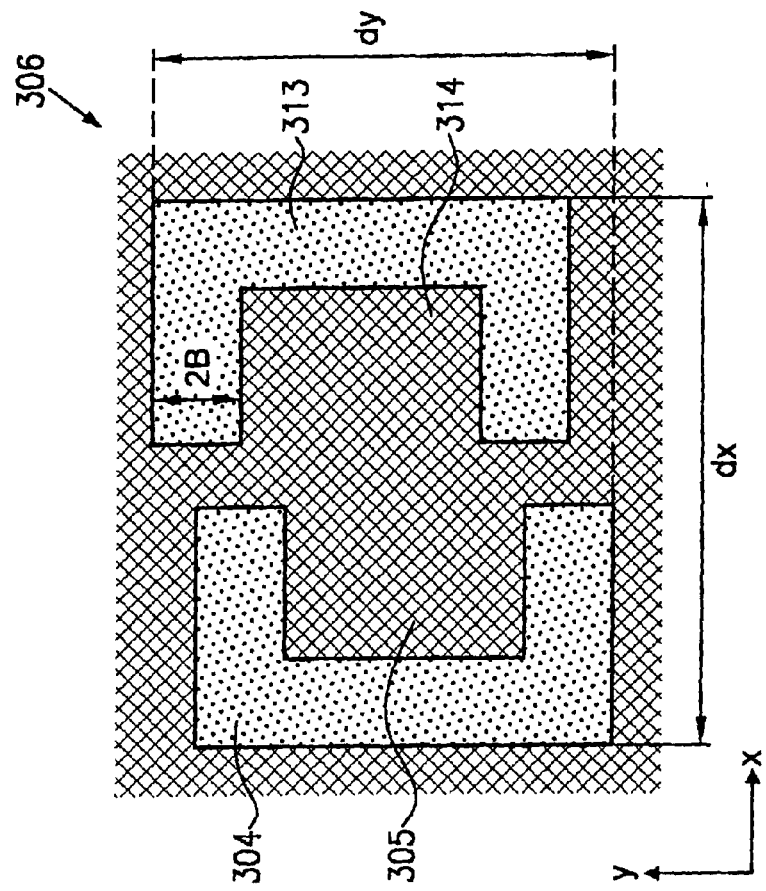
FIG. 3 shows a schematic top view of a further illustrative embodiment in accordance with the present invention.

FIG. 3 schematically shows a top view of a further illustrative embodiment in accordance with the present invention. In FIG. 3, an elementary cell 306 of a semiconductor structure comprises a first region 304 and a second region 305. The first and second regions 304, 305 have been formed in a first manufacturing step employing a first photolithographic process. Furthermore, the elementary cell 306 comprises a third region 313 and a fourth region 314 formed during a second manufacturing step including a second photolithographic process. In this illustrative embodiment, the regions 304 and 313, on the one side, and the regions 305 and 314 on the other side may be formed of materials with highly different optical characteristics, such as a highly different reflectivity. The regions 304 and 313 may, for example, be considered as slits or bars of a two-dimensional periodic array. The regions 304 and 313 then define a "grating pitch" DY in the Y direction and a corresponding "grating pitch" DX in the X direction, as indicated in FIG. 3. The regions 304 and 313 are offset from each other with respect to the X direction as well as with respect to the Y direction. Preferably, a width of a region 304 and 313 is larger than 2×B, wherein B is the maximum overlay error in the X and Y directions. Thus, the regions 304 and 313 are arranged such that the corresponding offsets in the Y and X directions are approximately B. A relative displacement of the regions 304 and 313 caused by an overlay error in the first and second manufacturing steps will independently lead to a variation of DY and DX. This arrangement is particularly advantageous when the apparatus used for analyzing the beam diffracted by the periodic structure of FIG. 3 comprises a spatial-resolving detector that allows the detection of intensity variations with respect to the X and Y directions. It should be noted that the geometric shape of regions 304 and 313 may be varied in numerous ways to be in conformity with corresponding design rules and design requirements regarding the first and second manufacturing steps.

In the following, a method will be described to determine an overlay error caused during the formation of a semiconductor structure involving two subsequent photolithographic processes. First, a semiconductor structure is provided having at least one two-dimensional diffracting area formed thereon. The diffracting area has been formed during a first and a second manufacturing step, including a first and second photolithographic process so that any overlay error occurring during the formation of the diffracting area is translated into the diffracting characteristics of the diffracting area. The semiconductor structures described with reference to FIGS. 1–3 may preferably be used for this purpose. Next, a light beam is directed onto the at least one diffracting area, wherein advantageously the light spot focused on the diffracting area is smaller in size than the diffracting area to avoid edge effects at a boundary between the diffracting area and the normal chip area and to facilitate central alignment of the light spot on the diffracting area. This "global" edge effect may not be confused with the "local" periodically within each elementary cell created edge effects caused by the X and Y overlaps.

As previously explained, preferably a diffracting area is formed in one or more regions of the semiconductor structure where no additional chip area for circuit features is occupied. Thus, a preferred location for the diffracting area is in the scribe lane. The diffracting area, however, may be provided at any arbitrary position within the semiconductor structure that is deemed to be appropriate to obtain the required overlay information. In particular, periodically arranged circuit features defining a two-dimensional periodic pattern formed in a process sequence including overlay-sensitive process steps may be employed as a diffracting area in so far as these periodically arranged circuit features are relatively positioned to each other to represent the magnitude and direction of the overlay error. For example, a photoresist layer may be patterned on top of a two-dimensional periodic circuit structure. This arrangement is advantageous for investigating the overlay error caused only by the photolithographical process independent from other patterning steps. After completion of the measurement and determination of the overlay accuracy of the lithography process, the photoresist layer may or may not, depending on design requirements, be removed.

The light beam directed on the diffracting area preferably includes a plurality of wavelengths and a defined polarization state, such as a light beam emitted by a spectroscopic ellipsometer, as is well known in the art of semiconductor manufacturing. Instead of a multi-wavelength beam, a monochromatic beam may be used and the angle of incidence may be varied within a predefined range. As in the case of an ellipsometer, the incident light beam may be linearly polarized, for example by means of a polarizor, but a non-polarized light beam may be used as well. The term "light beam" is intended to include a broad range of wavelengths that is appropriate for analyzing the diffracting characteristics of the two-dimensional diffracting area. Thus, the term "light beam" is intended to include radiation of a wavelength from a few millimeters to a few nanometers.

Next, the diffracted light beam is detected by a suitable detector, such as one or more photodiodes, CCD elements, or any other appropriate tool that is capable of detecting the intensity with respect to wavelength and/or angle of incidence. Moreover, the detector may be adapted to detect the polarization state of the diffracted beam. The detector may further comprise means to detect the intensity and/or the polarization state in a spatially resolved fashion. A correspondingly-equipped detector is particularly advantageous in combination with a semiconductor structure described in FIG. 3, since the spectral intensity distribution of the diffracted beam significantly varies with respect to the variation of DX and DY. The light source emitting the incident beam, the detector and the diffracting area are positioned to define a plane of incidence. Due to the two-dimensional periodicity of the diffracting area and the design of the diffracting area in accordance with the present invention, overlay information with respect to the X direction and the Y direction is contained in the diffracted beam independently from each other. Hence, the overlay error in the X and Y directions can be determined by one measurement step including only one alignment step for adjusting the incident beam to the diffracting area.

After detecting the diffracted beam, the measured spectrum and/or information extracted therefrom are compared to a corresponding reference spectrum and/or to corresponding reference data to determine the diffracting characteristics of the two-dimensional diffracting area, including information about the magnitude and the direction, i.e., the sign of the overlay error, with respect to two linearly independent directions, i.e., the X and Y directions. The reference data and/or reference spectra may be derived from a theoretical model, experimental data and/or a combination thereof.

Preferably, a plurality of two-dimensional diffracting areas are provided on the semiconductor structure at various places to monitor the overlay accuracy with respect to any inhomogeneities across the entire substrate surface. Advantageously, the plurality of two-dimensional diffracting areas is provided at various locations in the scribe lanes so as not to unnecessarily waste precious chip area.

In addition, the diffracted light beam is also analyzed with respect to critical dimensions of features forming the two-dimensional diffracting area such that required overlay information and information on the quality of features of critical dimensions is obtained simultaneously.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A semiconductor structure for metrology of critical dimensions and overlay accuracy, comprising:
    a substrate having a surface defined by an X-direction and a Y-direction;
    a first periodic pattern formed on the substrate and having a first X-periodicity along the X-direction and a first Y-periodicity along the Y-direction; and
    a second periodic pattern formed on the substrate and having a second X-periodicity along the X-direction and a second Y-periodicity along the Y-direction;
    wherein the first periodic pattern and the second periodic pattern overlap with each other to define an X-overlap region indicating an overlay error in the X-direction, and a Y-overlap region indicating an overlay error in the Y-direction.

2. The semiconductor structure of claim 1, wherein the first X-periodicity is defined by a first X-grating and the first Y-periodicity is defined by a first Y-grating.

3. The semiconductor structure of claim 1, wherein the first X-grating and the first Y-grating comprise lines and spaces extending along the X- and Y-directions, respectively.

4. The semiconductor structure of claim 2, wherein the first X-grating is formed by adjacent lines of different optical properties, and the first Y-grating is formed by adjacent lines of different optical properties.

5. The semiconductor structure of claim 4, wherein two adjacent lines of the X-grating and of the Y-grating are formed of a different material.

6. The semiconductor structure of claim 2, wherein the first X-periodicity is defined by adjacent first and second regions, wherein the first and second regions differ from each other in at least one of a shape, a type of material and a surface profile.

7. The semiconductor structure of claim 2, wherein the first Y-periodicity is defined by adjacent first and second regions, wherein the first and second regions differ from each other in at least one of a shape, a type of material and a surface profile.

8. The semiconductor structure of claim 1, wherein the second periodic pattern comprises first line portions and second line portions that are oriented in one of the X-direction and the Y-direction.

9. The semiconductor structure of claim 8, wherein the first line portions form a part of said X-overlap region for a predefined range of X-overlay errors, and wherein the second line portions form a part of said Y-overlap region for a predefined interval of Y-overlay errors.

10. The semiconductor structure of claim 5, wherein the second periodic pattern is a second grating.

11. The semiconductor structure of claim 10, wherein the first and second periodic patterns define a plurality of elementary cells, whereby each elementary cell comprises N first line portions, where N is an integer number equal or larger than 1.

12. The semiconductor structure of claim 11, wherein each elementary cell comprises at least one second line portions having a predefined length L, with L being smaller than a length of the first line portions.

13. The semiconductor structure of claim 12, wherein a ratio of N and L is selected to adjust the response of the first and second periodic patterns.

14. A semiconductor structure for metrology of critical dimensions and overlay accuracy, comprising:
   a substrate having a surface defined by an X-direction and a Y-direction;
   a two-dimensional periodic structure including a plurality of elementary cells, each elementary cell comprising:
      a first region and a second region that define a first edge extending along the X-direction, and a second edge extending along the Y-direction; and
      a third region formed in spaced relationship to the first and second regions, the third region defining a Y overlap region with the first and second regions at the first edge, and defining an X overlap region with the first and second regions at the second edge, wherein the X overlap region and the Y overlap region differ from each other in at least one of a shape, a total area, a diffracting characteristic, and an optical characteristic.

15. The semiconductor structure of claim 14, wherein at least one of the characteristics from the group of shape, total area, diffracting characteristics and optical characteristics of the X-overlap region is determined by an overlay error in the X-direction, and wherein at least one of the characteristics from the group of shape, total area, diffracting characteristics, and optical characteristics of the Y overlap region is determined by an overlay error in the Y-direction.

16. The semiconductor structure of claim 14, wherein at least one of the first, second and third regions comprises one or more recessed regions.

17. The semiconductor structure of claim 16, wherein said one or more recessed regions are openings.

18. The semiconductor structure of claim 14, wherein the third region is formed over the first and second regions.

19. The semiconductor structure of claim 14, further comprising a fourth region formed in the same material layer as the third region.

20. A semiconductor structure for metrology of critical dimensions and overlay accuracy comprising:
   a substrate having a surface defined by an X-direction and a Y-direction;
   a first periodic pattern formed above the substrate; and
   a second periodic pattern formed above the substrate;
   wherein the first and second periodic patterns overlap with each other and define a composed two-dimensional diffracting pattern having a pitch DX along the X-direction and a pitch DY along the Y-direction, DX and DY being determined by the relative position of the first and second periodic patterns.

21. The semiconductor structure of claim 20, wherein the first and second periodic patterns are formed in a first material layer and a second material layer, respectively.

22. The semiconductor structure of claim 21, wherein the first periodic pattern and the second periodic pattern are spaced apart along the X-direction by a distance determined by an overlay error between the first and the second material layer.

23. The semiconductor structure of claim 22, wherein the first and second periodic patterns are spaced apart along the Y-direction by a distance determined by an overlay error along the Y-direction.

* * * * *